US009695104B2

(12) United States Patent
Gigler et al.

(10) Patent No.: US 9,695,104 B2
(45) Date of Patent: Jul. 4, 2017

(54) PROCESS FOR RUTHENIUM-CATALYZED TRANSVINYLATION OF CARBOXYLIC ACIDS

(71) Applicant: Wacker Chemie AG, Munich (DE)

(72) Inventors: Peter Gigler, Dachau (DE); Maria Leute, Burghausen (DE); Jürgen Stohrer, Pullach (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 15/302,745

(22) PCT Filed: Mar. 23, 2015

(86) PCT No.: PCT/EP2015/056109
§ 371 (c)(1),
(2) Date: Oct. 7, 2016

(87) PCT Pub. No.: WO2015/154979
PCT Pub. Date: Oct. 15, 2015

(65) Prior Publication Data
US 2017/0036988 A1 Feb. 9, 2017

(30) Foreign Application Priority Data
Apr. 10, 2014 (DE) .......... 10 2014 206 916

(51) Int. Cl.
C07C 67/343 (2006.01)
C07C 67/10 (2006.01)
(Continued)

(52) U.S. Cl.
CPC ......... C07C 67/343 (2013.01); B01J 31/2208 (2013.01); C07C 51/09 (2013.01);
(Continued)

(58) Field of Classification Search
None
See application file for complete search history.

(56) References Cited

U.S. PATENT DOCUMENTS 4,981,973 A * 1/1991 Murray .................. C07C 41/16
548/229
5,155,253 A 10/1992 Murray
(Continued)

FOREIGN PATENT DOCUMENTS

EP 0351603 1/1990
EP 0497340 8/1992
(Continued)

OTHER PUBLICATIONS

International Search Report for PCT/EP2015/056109 dated May 28, 2015, 2 pages.
(Continued)

Primary Examiner — Yate K Cutliff
(74) Attorney, Agent, or Firm — RatnerPrestia

(57) ABSTRACT

The invention relates to a process for transvinylation of a carboxylic acid feedstock with a vinyl ester feedstock to obtain a vinyl ester product and the corresponding acid of the vinyl ester feedstock in the presence of one or more ruthenium catalysts, wherein a) the vinyl ester feedstock, the carboxylic acid feedstock and a ruthenium catalyst are fed to the reactor, and b) the transvinylation reaction is carried out, characterized in that a carbonyl-free Ru(III) carboxylate is used as the ruthenium catalyst and in that no carbon monoxide is supplied, c) the reaction is carried out at a temperature of 110 to 170° C., d) upon completion of the transvinylation reaction, the vinyl ester feedstock and the corresponding acid are separated from the reaction mixture by distillation, e) the vinyl ester product is separated by
(Continued)

distillation from the bottom product of the distillation, and
f) the remaining reaction mixture is recycled into the reactor.

11 Claims, 1 Drawing Sheet

(51) Int. Cl.
*C07C 51/09* (2006.01)
*B01J 31/22* (2006.01)
*C07C 51/353* (2006.01)

(52) U.S. Cl.
CPC ............ *C07C 51/353* (2013.01); *C07C 67/10* (2013.01); *B01J 2231/40* (2013.01); *B01J 2531/821* (2013.01)

(56) References Cited

U.S. PATENT DOCUMENTS 5,210,207 A 5/1993 Mokhtarzadeh et al.

2014/0343310 A1 11/2014 Johnen et al.
2014/0357881 A1 12/2014 Johnen et al.

FOREIGN PATENT DOCUMENTS

| EP | 0506070 | 9/1992 |
|----|---------|--------|
| EP | 0376075 | 6/1994 |
| WO | 9209564 | 6/1992 |
| WO | 2013117294 | 8/2013 |
| WO | 2013117295 | 8/2013 |

OTHER PUBLICATIONS

Ruthenium-Catalyzed Transvinylation—New Insights, Jennifer Ziriakus et al., 2013 Wiley-VCH Verlag GmbH & Co. KGaA, Weinheim, Adv. Synth. Catal. 2013, 355, pp. 2845-2859, asc.wiley-vch.de, 15 pages.

* cited by examiner

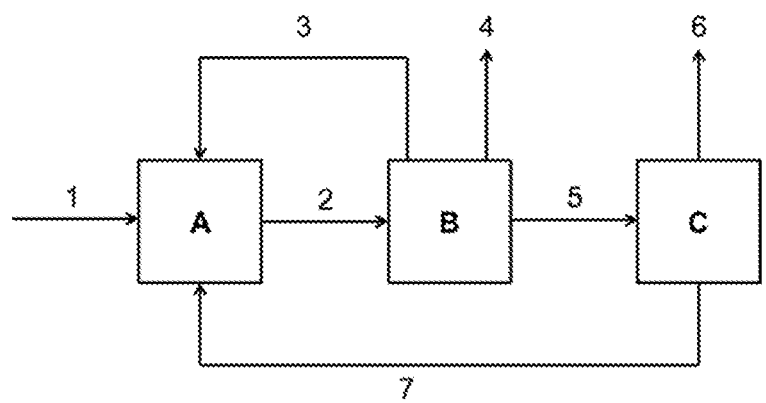

PROCESS FOR RUTHENIUM-CATALYZED TRANSVINYLATION OF CARBOXYLIC ACIDS

CROSS-REFERENCE TO RELATED APPLICATIONS

This application is a U.S. National Phase Application of PCT International Application PCT/EP2015/056109, filed Mar. 23, 2015, which claims priority benefit of German Application DE 10 2014 206 916.5, filed Apr. 10, 2014, the disclosures of which are incorporated herein in their entirety.

BACKGROUND

The invention relates to a process for transvinylation of a reactant carboxylic acid with a reactant vinyl ester to afford a product vinyl ester and the corresponding acid of the reactant vinyl ester in the presence of one or more ruthenium catalysts.

Transvinylation of carboxylic acids is used for preparing vinyl esters. This is to be understood as meaning the transfer of a vinyl unit from a reactant vinyl ester (1V) to a reactant carboxylic acid (2S) to generate a product vinyl ester (2V) and the corresponding acid of the reactant vinyl ester (1S).

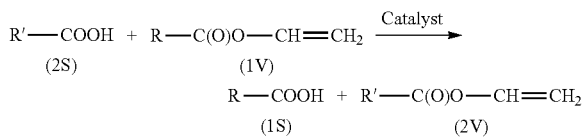

EP 376075 B1 discloses the transvinylation of vinyl esters with carboxylic acids in the presence of palladium catalyst, wherein copper bromide and special lithium compounds are employed as cocatalysts.

In addition to palladium catalyst and mercury catalysts, the prior art also employs ruthenium compounds as catalyst for transvinylation of vinyl esters with carboxylic acids. Ruthenium compounds are notable for their high solubility, low volatility and high thermal stability. This is coupled with a high, temperature-inducible activity.

EP 351603 A2 (=EP 506070, U.S. Pat. Nos. 4,981,973, 5,155,253) describes a process for transvinylation of carboxylic acids using various Ru compounds as catalysts. The authors postulate a $[Ru(CO)_2RCO_2]$ unit as the decisive structural element in the formation of the active species. Accordingly, all Ru compounds which may be converted into this structural element in situ may be employed as catalysts. Cited as a suitable starting species is, inter alia, the industrially available trinuclear Ru complex $[Ru_3O(OAc)_6(H_2O)_3]OAc$ and it is found that this carbonyl-free ruthenium carboxylate is also converted into the active catalyst species in a nitrogen atmosphere instead of a carbon monoxide atmosphere. This complex is employed as catalyst in the transvinylation of various carboxylic acids in examples 2, 5, 6 and 14. While the reaction in examples 2, 5 and 6 takes place in a carbon monoxide atmosphere and with reaction times of 3 or 4.5 hours, the transvinylation in example 14 is effected at 100° C. in a nitrogen atmosphere. The significantly longer reaction time of 19 hours is attributable to a retarded formation of the active catalyst species in the absence of carbon monoxide. The use of $[Ru_3O(OAc)_6(H_2O)_3]OAc$ in a continuous process is not described Adv. Synth. Catal. 2013, 355, 2845-2859 confirms the theory from EP 351603 A2 and postulates a $[Ru(CO)_3(RCO_2)_2]$ complex as active catalyst species. In this case the catalytically active species is formed on the basis of $RuCl_3$. Ru carbonyl propionate and Ru carbonyl valerate are produced by reaction of $RuCl_3$ with propionic acid or valeric acid. Carbonyl-free ruthenium carboxylates are not employed.

EP 497340 A2 (U.S. Pat. No. 5,210,207) describes a transvinylation process for preparing product vinyl esters having a higher boiling point than that of the reactant vinyl ester. Reactive distillation of at least one of the product components shifts the equilibrium of the reaction to the product side. It is preferable when the Ru catalysts described in EP 351603 A2 are used therefor. Example 8 employs $[Ru_3O(OAc)_6(H_2O)_3]OAc$ as catalyst, it being pointed out that the conversion is retarded compared to a Ru carbonyl carboxylate. This suggests that the conversion of the employed $[Ru_3O(OAc)_6(H_2O)_3]OAc$ into the active catalyst species is effected only slowly under the reaction conditions of example 8.

WO 92/09554 A1 describes a process where after the transvinylation the reaction mass is first separated and the product vinyl ester is then removed by azeotropic distillation. This process is aimed especially at separation of acid/vinyl ester mixtures having small differences in boiling point. The transvinylation reaction preferably employs Ru catalysts from EP 351603 A2. The examples do not describe the use of carbonyl-free ruthenium carboxylates as catalyst.

WO 2013/117294 A1 describes a continuous process for preparing vinyl carboxylate esters. The transition metal-catalyzed transvinylation is operated in a steady-state and the reaction mixture fractionated in a subsequent step. WO 2013/117295 describes a further implementation of this process comprising a subsequent derivatization of the conjugate acid of the reactant vinyl ester that is formed. The examples in both specifications employ predominantly Pd catalysts for the transvinylation. Two examples employ the Ru catalyst ruthenium dicarbonyl acetate. Carbonyl-free ruthenium carboxylate catalysts are not described.

The use of Ru catalysts in the transvinylation reaction entails clear advantages compared to Pd catalysts in terms of solubility, volatility, thermal stability and thermally inducible activity. Numerous Ru compounds can be converted into active Ru species in situ. On account of their large industrial scale availability, ruthenium(III) chloride and the trinuclear carbonyl-free Ru acetate complex $[Ru_3O(OAc)_6(H_2O)_n(AcOH)_{3-n}]OAc$ where n=0 to 3 or its (solvent-free) analog $[Ru_3O(OAc)_6]OAc$ especially are advantageous. While the first-mentioned of these must first be formed by addition of a base, the Ru acetate complex of the prior art requires a carbon monoxide atmosphere in order to be converted into the active species within short reaction times. However, the avoidance of a carbon monoxide supply is highly desirable for reasons of safety engineering. A process in which a commercially available catalyst is converted into the active species without addition of carbon monoxide within short reaction times and which is thus suitable for use in continuous transvinylation processes has not hitherto been disclosed.

SUMMARY

The problem addressed by the present invention was therefore that of developing a transvinylation process where the employed catalyst is converted into the catalytically active species within the residence time in the reaction zone without addition of carbon monoxide.

The invention provides a process for transvinylation of a reactant carboxylic acid with a reactant vinyl ester to afford a product vinyl ester and the corresponding acid of the reactant vinyl ester in the presence of one or more ruthenium catalysts, wherein a) the reactant vinyl ester, the reactant carboxylic acid and a ruthenium catalyst are supplied to the reactor, and b) the transvinylation reaction is performed, characterized in that the ruthenium catalyst employed is a carbonyl-free Ru(III) carboxylate and no carbon monoxide is supplied, c) the reaction is performed at a temperature of 110° C. to 170° C., d) after completion of the transvinylation reaction the reactant vinyl ester and the corresponding acid are distillatively removed from the reaction mixture, and e) the product vinyl ester is distillatively removed from the bottoms product of the distillation, and f) the remaining reaction mixture is recycled into the reactor.

BRIEF DESCRIPTION OF THE DRAWINGS

The FIGURE is a flow diagram of an embodiment of the process according to the invention.

DETAILED DESCRIPTION

The FIGURE depicts the basic procedure of the process according to the invention. The reactants (1) are supplied to a reactor (A) individually or as a mixture. The transvinylation reaction is effected in the reactor (A). The resultant reaction mixture (2) is freed from reactant vinyl ester (3) and the corresponding acid thereof (4) in a distillation apparatus (B). The reactant vinyl ester (3) is optionally recycled into the reactor (A). The product vinyl ester (6) is then completely or partially removed from the remaining product mixture (5) in a distillation apparatus (C). The residual catalyst-containing reaction bottoms (7) are recycled into the reactor (A) and the catalyst is thus reused.

Reactors usable as reactor (A) include stirred tanks, stirred tank cascades or tubular reactors. It is preferable when the reactor (A) is a tubular reactor.

Chemistries employable as the reactant vinyl ester are any desired vinyl carboxylate esters of general formula R—C(O)O—CH=CH$_2$, wherein R may be an aliphatic radical having 1 to 12 carbon atoms or may be a cycloaliphatic radical having up to 12 carbon atoms or may be an aromatic radical having up to 12 carbon atoms. Preference is given to the use of low molecular weight reactant vinyl esters, wherein R is an alkyl radical having 1 to 6 carbon atoms, for example vinyl acetate, vinyl propionate and vinyl pivalate. Particular preference is given to the use of vinyl acetate.

Also supplied to the reactor is at least one reactant carboxylic acid of general formula R'—COOH, wherein R' may be an aliphatic radical having 1 to 22 carbon atoms or may be a cycloaliphatic radical having up to 22 carbon atoms or may be an aromatic radical having up to 22 carbon atoms. It is preferable to employ reactant carboxylic acids of the recited compound classes having 6 to 18 carbon atoms. Examples thereof are caproic acid, cyclohexanecarboxylic acid, n-heptanoic acid, 2-methylhexanoic acid, 2-ethylhexanoic acid, n-octanoic acid, n-nonanoic acid, isononanoic acid, neononanoic acid, n-decanoic acid, neodecanoic acid, lauric acid, myristic acid, palmitic acid, stearic acid, benzoic acid, naphthalenecarboxylic acid. Particular preference is given to Versatic acids$^R$ (alpha-branched carboxylic acids having 9 to 12 carbon atoms from Momentive) or neo acids having 9 to 12 carbon atoms and fatty acids such as lauric acid, myristic acid, palmitic acid, stearic acid.

The catalyst employed is a carbonyl-free Ru(III) carboxylate. Addition may be in solid and dissolved form. The carbonyl-free Ru(III) carboxylate is preferably employed in dissolved form. Carboxylates that may be employed are carboxylates of carboxylic acids of general formula R"—COOH, wherein R" may be an aliphatic radical having 1 to 22 carbon atoms or may be a cycloaliphatic radical having up to 22 carbon atoms or may be an aromatic radical having up to 22 carbon atoms. Examples thereof are the carboxylates of the following carboxylic acids: acetic acid, propionic acid, n-butyric acid, isobutyric acid, n-valeric acid, 2-methylbutyric acid, 3-methylbutyric acid, pivalic acid, caproic acid, cyclohexanecarboxylic acid, n-heptanoic acid, 2-methylhexanoic acid, 2-ethylhexanoic acid, n-octanoic acid, n-nonanoic acid, isononanoic acid, neononanoic acid, n-decanoic acid, neodecanoic acid, lauric acid, myristic acid, palmitic acid, stearic acid, benzoic acid and naphthalenecarboxylic acid. The use of a ruthenium Ru(III) acetate is preferred.

The carbonyl-free Ru(III) carboxylates are commercially available, for example the Ru(III) carboxylate of formula [Ru$_3$O(OAc)$_6$(H$_2$O)$_n$(AcOH)$_{3-n}$]OAc where n=0 to 3 or of formula [Ru$_3$O(OAc)$_6$]OAc, wherein Ac stands for a CH$_3$—C=O radical in each case. The recited carbonyl-free Ru(III) carboxylates also obtainable by reaction of RuCl$_3$ with the relevant carboxylic acid by processes known to one skilled in the art. [Ru$_3$O(OAc)$_6$(H$_2$O)$_n$(AcOH)$_{3-n}$]OAc where n=0 to 3 or [Ru$_3$O(OAc)$_6$]OAc may for example be obtained by reaction of RuCl$_3$ with acetic acid and sodium acetate in ethanol.

Suitable solvents are the carboxylic acids just described. The use of acetic acid is preferred. The concentration of the carbonyl-free Ru(III) carboxylate in the solvent may be 0.01 to 50 wt %, preferably 0.1 to 20 wt %, particularly preferably 1 to 10 wt %.

It is particularly preferable to employ a solution of Ru(III) acetate in acetic acid and most preferable to employ a solution, in each case in acetic acid, of [Ru$_3$O(OAc)$_6$(H$_2$O)$_n$(AcOH)$_{3-n}$]OAc where n=0 to 3 or Ru$_3$O(OAc)$_6$]OAc.

The ruthenium catalyst is typically employed in concentrations of 0.1 to 10 000 ppm (content of ruthenium based on the reaction mass composed of reactant vinyl ester and reactant carboxylic acid) and preference is given to the use of 1 to 1000 ppm (content of ruthenium based on the reaction mass composed of reactant vinyl ester and reactant carboxylic acid).

A polymerization inhibitor may optionally be added to the reactants. It is preferable when 100 to 10 000 ppm, based on the reaction mass composed of reactant vinyl ester and reactant carboxylic acid, of polymerization inhibitor are employed. Examples of polymerization inhibitors are hydroquinone, methoxyhydroquinone, tertiary-butyl catechol, phenothiazine or nitroxide radicals such as TEMPO or 4-OH-TEMPO (TEMPO=2,2,6,6-tetramethylpiperidinyloxyl). The use of phenothiazine or hydroquinone is preferred.

An anhydride of the respective reactant carboxylic acid may optionally also be added as a reactant. The optionally supplied anhydrides of the reactant carboxylic acid of general formula R$^1$—C(O)—O—C(O)—R$^2$ may be mixed (R$^1$≠R$^2$) or symmetric (R$^1$=R$^2$) anhydrides, wherein R$^1$ and $R^2$ each represent an aliphatic radical having 1 to 22 carbon atoms or a cycloaliphatic radical having up to 22 carbon atoms or an aromatic radical having up to 22 carbon atoms. Examples thereof are mixed or symmetric anhydrides of the following acids: acetic acid, propionic acid, n-butyric acid, isobutyric acid, n-valeric acid, 2-methylbutyric acid, 3-methylbutyric acid, pivalic acid, caproic acid, cyclohexanecarboxylic acid, n-heptanoic acid, 2-methylhexanoic acid, 2-ethylhexanoic acid, n-octanoic acid, n-nonanoic acid, isononanoic acid, neononanoic acid, n-decanoic acid, neodecanoic acid, lauric acid, myristic acid, palmitic acid, stearic acid, benzoic acid and naphthalenecarboxylic acid. Preference is given to employing the symmetrical anhydrides of the reactant carboxylic acid.

To achieve transvinylation the reactants reactant vinyl ester, reactant carboxylic acid and Ru catalyst and optionally inhibitor and optionally anhydride of the reactant carboxylic acid may be supplied to the reactor individually or in a mixture.

The molar ratio of reactant vinyl ester to reactant carboxylic acid may be from 1:10 to 10:1. Preference is given to a ratio of reactant vinyl ester to reactant carboxylic acid of 1:2 to 8:1, particular preference being given to a ratio of 1:1 to 6:1.

The transvinylation is generally performed at a temperature of 110° C. to 170° C., preferably at a temperature of 120° C. to 150° C. The pressure at which the transvinylation is effected depends on the temperature and is generally ≥2 bar abs., preferably 5 to 15 bar abs. and most preferably 5 to 10 bar abs. The reaction is performed without supplying carbon monoxide and preferably in a protective gas atmosphere, for example nitrogen, in a manner known per se.

In the process according to the invention the residence time in the reactor is generally 0.25 to 5 hours, preferably 1 hour to 4 hours.

In contrast to a reactive distillation in the process according to the invention the fractionation of the product mixture obtained is effected only after completion of the transvinylation preferably by distillation in appropriate distillation columns.

The pressure and temperature of the distillation and the configuration of the distillation columns depend on the components present in the product mixture and may be determined by one skilled in the art by routine tests for example. Accordingly, no reactive distillation or azeotropic distillation is performed in the process according to the invention.

In the fractionation of the product mixture the unconverted remaining reactant vinyl ester and the corresponding acid thereof are respectively removed from the product mixture in a first step. The thus obtained reactant vinyl ester may optionally be recycled into the reactor for renewed transvinylation. The thus obtained corresponding acid of the reactant vinyl ester may be employed as a reactant in other chemical processes; for example for producing vinyl acetate in the case of acetic acid.

In a preferred embodiment the product vinyl ester is at least partly or completely removed by distillation from the product mixture remaining after removal of the reactant vinyl ester and the corresponding acid thereof. The resulting reaction bottoms which can comprise reactant carboxylic acid, anhydrides of the reactant carboxylic acid, ruthenium catalyst and optionally further components such as product vinyl ester or polymeric constituents are recycled into the reactor with addition of fresh reactants and optionally fresh carbonyl-free Ru(III) carboxylate for renewed transvinylation.

The addition of fresh reactants and optionally fresh carbonyl-free Ru(III) carboxylate into the reactor for renewed transvinylation may respectively be effected in admixture with the recycled reaction bottoms or may respectively be effected seperately from the recycled reaction bottoms.

The substeps of the process, both the transvinylation and the workup steps, may be performed in batchwise, semicontinuous and continuous fashion. The process is preferably carried out in continuous fashion.

The process according to the invention allows carbonyl-free Ru(III) carboxylate complexes to be employed as catalysts in the transvinylation of carboxylic acids. It has been found that, surprisingly, the Ru carboxylate species may be converted into the active species at temperatures of ≥110° C. even at residence times in the reaction zone of less than 5 h.

The process according to the invention renders a carbon monoxide supply unnecessary. The use of commercially available catalysts in continuous transvinylation processes is further made possible.

EXAMPLES the examples which follow serve to more particularly elucidate the invention.

The reported conversions relate in all cases to the starting component reactant carboxylic acid (2S) or reactant vinyl ester (1V) that is employed in a lesser molar fraction. The conversion is defined as $U(\%)=100\times(n_0-n_E)/n_0$, wherein $n_0$ is the amount of substance of the starting component at the beginning of the reaction and $n_E$ is the amount of substance at the end of the reaction.

Comparative Example 1

Transvinylation with Ru acetate solution as catalyst at 100° C.

In a 100 mL Berghoff autoclave 25.0 g (125 mmol) of lauric acid, 43.0 g (500 mmol) of vinyl acetate and 0.69 g (0.9 mmol) of $[Ru_3O(OAc)_6(H_2O)_3]OAc$ (4.5 wt % Ru, dissolved in acetic acid from Umicore) were heated to 100° C. at 2.0 bar abs. for 6 hours.

Example 2

Transvinylation with Ru acetate solution as catalyst at 140° C.

In a 100 mL Berghoff autoclave 25.0 g (125 mmol) of lauric acid, 43.0 g (500 mmol) of vinyl acetate and 0.69 g (0.9 mmol) of $[Ru_3O(OAc)_6(H_2O)_3]OAc$ (4.5 wt % Ru, dissolved in acetic acid from Umicore) were heated to 140° C. at 6.0 bar abs. for 5 hours.

In both cases samples were taken at defined time intervals and the molar fractions in the reaction mixture required for calculating conversion were determined by means of quantitative NMR spectroscopy.

| | Lauric acid conversion [%] | |
| --- | --- | --- |
| Time [h] | comp. ex. 1 100° C. | ex. 2 140° C. |
| 0 | 0 | 0 |
| 1.5 | 0.9 | 78.4 |
| 3 | 1.6 | 79.7 |
| 4.5 | 2.6 | 79.3 |

The example shows that when ruthenium acetate solution is used as catalyst at a temperature of 140° C. the catalytically active species is formed within residence times of less than 5 hours. The equilibrium state is reached after as little as 1.5 hours.

The invention claimed is:

1. A process for transvinylation of a reactant carboxylic acid with a reactant vinyl ester to afford a product vinyl ester and a corresponding acid of the reactant vinyl ester in the presence of one or more ruthenium catalysts, the processing comprising:
   a) supplying a reaction mixture comprising the reactant vinyl ester, the reactant carboxylic acid and a ruthenium catalyst to a reactor,
   b) performing the transvinylation reaction at a temperature of 110° to 170° C.,
   wherein the ruthenium catalyst employed is a carbonyl-free Ru(III) carboxylate and no carbon monoxide is supplied,
   c) removing the reactant vinyl ester and the corresponding acid after completion of the transvinylation reaction by distillation from the reaction mixture forming a bottoms product,
   d) removing the product vinyl ester by distillation from the bottoms product of the distillation, and
   e) recycling the remaining reaction mixture into the reactor.

2. The process as claimed in claim 1, wherein the residence time in the reaction zone is 0.25 to 5 hours.

3. The process as claimed in claim 1, wherein the reaction is performed at a temperature of 120° C. to 150° C.

4. The process as claimed in claim 1, wherein the ruthenium catalyst employed is $[Ru_3O(OAc)_6(H_2O)_n(AcOH)_{3-n}]OAc$ where n=0 to 3 or $[Ru_3O(OAc)_6]OAc$.

5. The process as claimed in claim 4, wherein the ruthenium catalyst employed is a solution, in each case in acetic acid, of $[Ru_3O(OAc)_6(H_2O)_n(AcOH)_{3-n}]OAc$ where n=0 to 3 or $[Ru_3O(OAc)_6]OAc$.

6. The process as claimed in claim 1, wherein the reactant vinyl ester employed is a vinyl carboxylate ester of general formula $R-C(O)O-CH=CH_2$, wherein R is an aliphatic radical having 1 to 12 carbon atoms or is a cycloaliphatic radical having up to 12 carbon atoms or is an aromatic radical having up to 12 carbon atoms.

7. The process as claimed in claims 1, wherein the reactant vinyl ester employed is vinyl acetate.

8. The process as claimed in claim 1, wherein the reactant carboxylic acid employed is a carboxylic acid of general formula R'—COOH, wherein R' is an aliphatic radical having 1 to 22 carbon atoms or is a cycloaliphatic radical having up to 22 carbon atoms or is an aromatic radical having up to 22 carbon atoms.

9. The process as claimed in claim 1 wherein the reactant carboxylic acid employed is a carboxylic acid selected from the group consisting of alpha-branched carboxylic acids having 9 to 12 carbons atoms, neo acids having 9 to 12 carbon atoms, and fatty acids.

10. The process as claimed in claims 1, wherein an anhydride of the respective reactant carboxylic acid is added as a reactant.

11. The process as claimed in claim 9 wherein the fatty acids are selected from the group consisting of lauric acid, myristic acid, palmitic acid and stearic acid.

* * * * *